(12) United States Patent
Speck et al.

(10) Patent No.: US 10,596,303 B2
(45) Date of Patent: Mar. 24, 2020

(54) DRUG-ELUTING MEDICAL DEVICE

(71) Applicant: Invatec Technology Center GMBH, Frauenfeld (CH)

(72) Inventors: Ulrich Speck, Frauenfeld (CH); Silvio Schaffner, Frauenfeld (CH); Magdalena Renke-Gluszko, Frauenfeld (CH)

(73) Assignee: Invatec Technology Center GMBH, Frauenfeld (CH)

( * ) Notice: Subject to any disclaimer, the term of this patent is extended or adjusted under 35 U.S.C. 154(b) by 0 days.

(21) Appl. No.: 16/042,598

(22) Filed: Jul. 23, 2018

(65) Prior Publication Data

US 2019/0015562 A1   Jan. 17, 2019

Related U.S. Application Data

(63) Continuation of application No. 15/440,960, filed on Feb. 23, 2017, now Pat. No. 10,029,032, which is a continuation of application No. 13/143,703, filed as application No. PCT/EP2010/050162 on Jan. 8, 2010, now abandoned.

(60) Provisional application No. 61/159,503, filed on Mar. 12, 2009.

(30) Foreign Application Priority Data

Jan. 9, 2009 (IT) .............................. MI2009A0014

(51) Int. Cl.
   *A61L 29/16* (2006.01)
   *A61L 29/06* (2006.01)
   *A61M 25/10* (2013.01)

(52) U.S. Cl.
   CPC .............. *A61L 29/16* (2013.01); *A61L 29/06* (2013.01); *A61M 25/1002* (2013.01); *A61M 25/1029* (2013.01); *A61L 2300/216* (2013.01); *A61L 2300/416* (2013.01); *A61L 2300/602* (2013.01); *A61L 2300/63* (2013.01); *A61M 2025/1004* (2013.01); *A61M 2025/105* (2013.01); *A61M 2025/1031* (2013.01)

(58) Field of Classification Search
   None
   See application file for complete search history.

(56) References Cited

U.S. PATENT DOCUMENTS

| 6,858,644 | B2 | 2/2005 | Benigni et al. |
| 2006/0020243 | A1 | 1/2006 | Speck et al. |
| 2007/0178136 | A1 | 8/2007 | Arney et al. |
| 2008/0255510 | A1 | 10/2008 | Wang |
| 2010/0179475 | A1 | 7/2010 | Hoffmann et al. |
| 2011/0295200 | A1 | 12/2011 | Speck et al. |
| 2017/0173220 | A1 | 6/2017 | Speck et al. |

FOREIGN PATENT DOCUMENTS

| EP | 1857127 A1 | 11/2007 |
| WO | WO 2004/043532 A1 | 5/2004 |
| WO | WO 2007/106441 A2 | 9/2007 |
| WO | WO 2008/086794 A2 | 7/2008 |
| WO | WO 2008/089730 A2 | 7/2008 |
| WO | WO 2009/018816 A2 | 2/2009 |

OTHER PUBLICATIONS

International Search Report and Written Opinion for PCT Application PCT/EP2010/050162, dated Mar. 11, 2011, 17 pages.
International Preliminary Report on Patentability for PCT Application PCT/EP2010/050162, dated Jul. 12, 2011, 11 pages.
Office Action for European Patent Application No. 15158846.4, dated Sep. 20, 2018, 6 pages.
Office Action for Indian Patent Application No. 2847/KOLNP/2011, dated Aug. 13, 2018, 6 pages.
Hearing Notice and Objections for Indian Patent Application No. 2847/KOLNP/2011, dated Jul. 17, 2019, 3 pages.

*Primary Examiner* — Robert A Wax
*Assistant Examiner* — Randeep Singh

(57) ABSTRACT

The present invention relates to a drug-eluting medical device, in particular a balloon for angioplasty catheters with drug elution to prevent the restenosis of the vessel subjected to angioplasty. More particularly, the present invention relates to a catheter balloon completely or partially coated with paclitaxel in hydrated crystalline form or in hydrated solvated crystalline form, having an immediate release and bioavailability of a therapeutically effective amount of paclitaxel at the site of intervention. The balloon can be made of a polyether-polyamide block copolymer, or a polyester amide, or polyamide-12.

20 Claims, 1 Drawing Sheet

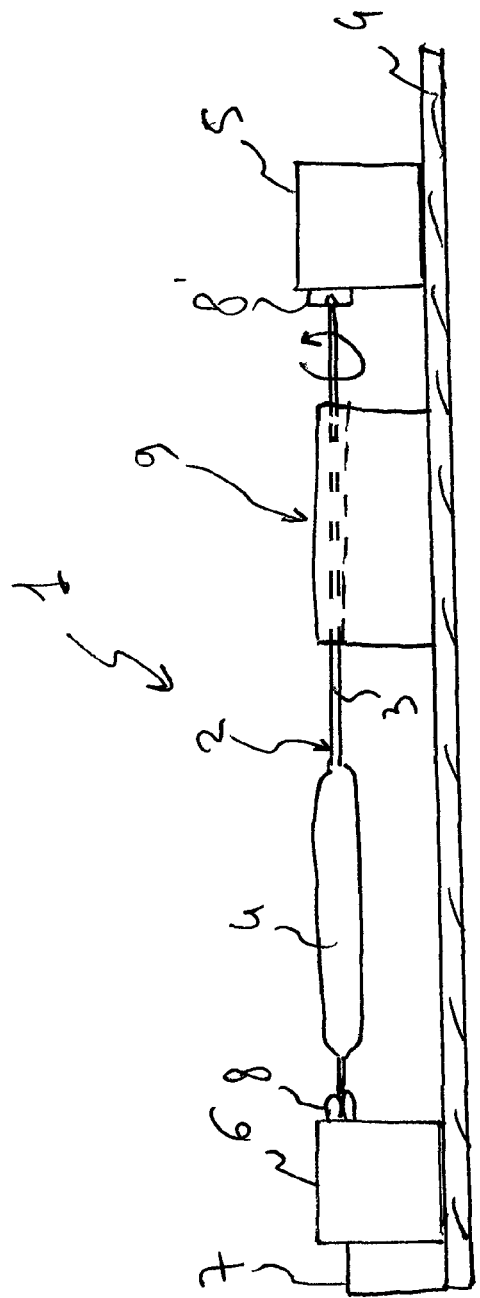

DRUG-ELUTING MEDICAL DEVICE

This application is a continuation of U.S. patent application Ser. No. 15/440,960, filed on Feb. 23, 2017, which is a continuation of U.S. patent application Ser. No. 13/143,703, having a U.S.C. 371(c) date of Aug. 18, 2011. U.S. patent application Ser. No. 13/143,703 is a U.S. National Stage Application of International Application No. PCT/EP2010/050162, which claims priority to U.S. Provisional Patent Application No. 61/159,503, filed on Mar. 12, 2009 and Italian Patent Application No. MI2009A000014, filed on Jan. 9, 2009.

The present invention relates to a drug-eluting medical device, in particular a balloon for angioplasty catheters with drug elution to prevent restenosis of the vessel subjected to angioplasty.

BACKGROUND OF THE INVENTION

The treatment of vascular atherosclerotic lesions is a widespread therapy. Such lesions are most often localized at predetermined portions of the blood vessels, of which they cause constrictions or also obstructions. Vascular atherosclerotic lesions are typically treated in angioplasty procedures by means of catheters provided with a balloon.

A catheter provided at the distal end thereof with a balloon is advanced, following a guidewire, to the ostium of the narrowed artery. Once the balloon has been arranged at the artery narrowing, it is repeatedly inflated and deflated. The insufflation, with successive deflation, of the balloon within the artery reduce the extent of the arterial luminal narrowing, and restore a suitable blood flow in the cardiac area, suffering from the stenosis. In some cases, it is necessary to arrange a so-called stent, which provides to maintain the artery patent also after withdrawal of the catheter and the balloon.

In both cases, success of the intervention is not complete. In fact, after a few months, some patients develop a new narrowing of the vessel wall at the intervention point. Such narrowing, known under the name of restenosis, is not due to the formation of new atherosclerotic plaques, but to a cell hyperproliferation process, particularly of the vascular smooth muscle cells, probably due to the dilating action operated by the foreign body, stent or balloon.

It has been observed that restenosis can be treated by coating a stent with a drug having antiproliferative action. Among the drugs usually employed to such aim, paclitaxel (taxol) has proved to be particularly efficient. The drug must be released for a sufficiently long time span, so as to inhibit the cell hyperproliferation process caused by the constant presence of the stent implanted in the vessel. However, the drug also induces an inhibition of the stent endothelization process, which is crucial to avoid the formation of thrombi. For this reasons, the use of a stent with drug elution ("drug eluting stent") has some drawbacks.

More recently, antiproliferative drug-coated catheter balloons have been proposed. However, in almost all cases, forms of slow release of the drug at the site of intervention after the drug has been transferred from the balloon to the vessel wall have been described.

However, it has been noticed that a drug elution over a prolonged time frame to inhibit the restenosis phenomenon is neither necessary nor desirable, but that it is sufficient, and rather more convenient, a time limited contact between drug and vessel surface, for example, from a few seconds to one minute. These are typically the contact times of a catheter balloon as described before.

The patent publication WO 02/076509 discloses drug-coated catheter balloons releasing such drug in an immediately bioavailable form during the short contact time of the balloon with the vessel wall.

It will be recognized that an approach such as the one described herein above poses completely different problems compared to those previously dealt with. In fact, while a prolonged drug elution can be obtained by various solutions, such as, for example, incorporation of the drug in a polymeric matrix or microcapsules, the immediate release will depend on several factors, of which the main ones are:

The nature of the drug, in particular the hydrophilicity or hydrophobicity thereof;

The form in which the drug is administered, in particular, the crystalline or amorphous form thereof;

The presence of possible excipients or "enhancers";

Optionally, the nature of the balloon surface on which the drug is deposited.

In fact, it should be understood that the drug has to be, first of all, released from the balloon to the vessel wall in the very short contact time available during an angioplasty procedure. Once the drug has been released, it has to be absorbed by the cell wall, before the blood flow washes it off. Ideally, it is therefore desirable that the drug absorption occurs concomitantly to the release thereof from the balloon.

However, it is just as well necessary that the drug is retained by the balloon surface in a manner sufficient to resist to all the handling operations which it is subjected to, both during the production step and during the preparation and carrying out of the angioplasty procedure, in any case, before the balloon reaches the site of intervention. This requires a perfect balance of such properties.

Therefore, it is an object of the present invention to provide a catheter balloon coated with a drug which allows an immediate release and bioavailability of the drug at the site of intervention.

It is a further object of the present invention to provide a method of coating of a catheter balloon with a drug in order to reach a good adherence of the drug on the balloon surface and at the same time a fast release of the drug upon contact of the said balloon surface with a blood vessel wall.

SUMMARY OF THE INVENTION

The present invention relates to a catheter balloon coated with paclitaxel in crystalline hydrated form, having an immediate release and bioavailability of the drug at the site of intervention.

A further object of the invention is a catheter balloon coated with paclitaxel in crystalline hydrated solvated form, having an immediate release and bioavailability of the drug at the site of intervention.

According to another aspect of the invention, the catheter balloon coated with paclitaxel in crystalline hydrated or solvated hydrated form as defined before is made of a polyether-polyamide block copolymer, or "compound" thereof with a polyamide.

According to a further aspect, the catheter balloon coated with paclitaxel in crystalline hydrated or solvated hydrated form as defined before is made of a polyester amide.

According to a further aspect, the catheter balloon coated with paclitaxel in crystalline hydrated or crystalline solvated hydrated form as defined before is made of polyamide-12.

According to a further aspect, the catheter balloon surface is hydrophilic or made hydrophilic by treatment with a hydrophilizing agent.

According to a further aspect of the invention, paclitaxel in crystalline hydrated or solvated hydrated form as defined before is deposited from a urea-containing solution.

According to an aspect of the invention, the balloon is inflated before coating with the paclitaxel solution and then it is folded when still wet. According to a further aspect of the invention, the balloon is folded, then it is inflated before coating with the paclitaxel solution and it is finally folded again when still wet.

BRIEF DESCRIPTION OF THE DRAWINGS

FIG. 1 shows a schematic side view of a device for rotating a catheter balloon during coating, according to an aspect of the invention.

DESCRIPTION OF THE INVENTION

The present invention relates in particular to a catheter balloon completely or partially coated with paclitaxel in hydrated crystalline form, having an immediate release and bioavailability of a therapeutically effective amount of paclitaxel at the site of intervention.

By the term "an immediate release and bioavailability" is meant a release from the balloon surface in periods of time ranging between 1 second and 1.5 minutes, preferably between 20 seconds and 1 minute, and an absorption by the vascular tissue in periods of time ranging between 1 second and 25 minutes, preferably between 20 seconds and 25 minutes.

By the term "therapeutically effective amount" is meant a drug amount capable of inducing a therapeutical or preventive effect against the restenosis of the treated vascular tissue in the patient.

By the term "site of intervention" is meant the section of the blood vessel treated directly with the catheter balloon of the invention, and the adjacent portion of the tissues in which the post-procedure presence of paclitaxel can be detected. Generally, such section will extend for 2-10 mm down- and upstream the contact section with the balloon.

With "paclitaxel in hydrated crystalline form" is meant paclitaxel with 2, 3 or 4 molecules of water of crystallization.

This crystalline form of paclitaxel can be obtained by dissolving paclitaxel in an aqueous solvent, by completely or partially wetting the balloon surface with such solution, and by letting the solvent to evaporate to a formation of a crystalline layer having a white, homogeneous, or partially inhomogeneous appearance.

As the aqueous solvent, a mixture of solvents selected from acetone/ethanol/water, tetrahydrofuran/water, methanol/water, acetone/water, ethanol/water, acetonitrile/water, DMF/water is preferably used. More preferably, the solvent is a 9:1 tetrahydrofuran/water mixture or a tetrahydrofuran/water mixture with ratios ranging between 9.5:0.5 and 65:35, or an acetone/ethanol/water mixture in which the organic solvent is present in amounts not less than 50% by volume relative to water.

The concentration of paclitaxel in the solution may range from 4 to 6 mg/ml, preferably about 5 mg/ml.

The balloon wetting step can be performed in several ways, known to those skilled in the art, such as, for example, dipping the balloon into the paclitaxel solution, spraying the paclitaxel solution on the balloon, or depositing the paclitaxel solution on the balloon by means of a syringe, a micropipette, or other similar dispensing device.

The balloon can be wetted with the paclitaxel solution in a deployed and inflated condition, or in a folded condition. It has been observed that in this second case also, the paclitaxel solution penetrates by capillarity under the folds, so as to form a drug depot which remains protected during the introduction step of the folded balloon into the blood vessel by means of the catheter, until reaching the site of intervention and the inflation thereof.

Methods are also known to selectively coat the area under the balloon folds, leaving the outer surface substantially free from the drug. Such methods can comprise, for example, the introduction into the balloon folds of a cannula bearing a series of micro-nozzles, through which the paclitaxel solution is deposited on the inner surface of the folds. Such a method is described, for example, in the international application No. PCT/IT2007/000816, filed on Nov. 21 2007, the contents of which are incorporated herein by reference.

The folded balloon will preferably have 3 to 6 folds.

A preferred wetting method for the balloon is the deposition of the paclitaxel solution on the folded balloon surface by means of a syringe, micropipette, or other similar dispensing means. Typically, the dispensing means will be made to slide on the surface from an end to the other one, and vice versa, while rotating the balloon around the longitudinal axis thereof, so as to establish a zigzag path. Alternatively, the dispensing means will be made to slide on the balloon surface starting from a substantially central position relative to the longitudinal extent thereof, and it will be made to slide towards a first end thereof and, subsequently, towards the second end thereof, so as to establish a substantially zigzag path.

According to a further method, the following steps are performed:
(a) Providing a balloon;
(b) Inflating the said balloon to a predetermined pressure;
(c) Coating the said inflated balloon of step
(b) with a paclitaxel solution;
(d) Deflating the coated balloon of step (c);
(e) Folding the deflated balloon of step (d) when still wet;
(f) Optionally, applying to the said folded balloon a protective cover.

According to this method the coating step is performed directly during the manufacturing process of the balloon catheter and the coating step is indeed part of the balloon catheter manufacturing process. Therefore, the production of a coated balloon catheter according to this method is advantageously quicker.

According to a further preferred method, the following steps are performed:
(g) Providing a folded balloon, for example a balloon having 3 or 6 folds;
(h) Inflating the said folded balloon to a predetermined pressure;
(i) Coating the said inflated balloon of step
(h) with a paclitaxel solution;
(j) Deflating the coated balloon of step (i);
(k) Re-folding the deflated balloon of step (j) when still wet;
(l) Optionally, applying to the said re-folded balloon a protective cover.

The use of an already folded balloon according to step (g) is advantageous because the material may keep some memory of the folds even after inflation in step (h), so that the subsequent re-folding of step (k) can take place easily and in a short time, without manipulating too much the coated balloon.

The said predetermined pressure in step (b) or (h) is a pressure below the nominal pressure (RBP pressure) of the balloon. For example, for balloon diameters between 4 and 7 mm and balloon length between 40 and 80 mm, the said predetermined pressure is between 5 and 9 bar.

The inflated balloon of step (b) or (h) is preferably disconnected from the pressurised air source before coating. In such a way, the balloon is still inflated, but it is not tensioned and the coating step advantageously benefits from this state condition. In the case of long balloons, inflation step (b) or (h) is prolonged for less than 1 minute.

Coating of step (c) or (i) is preferably performed by delivering the drug solution over the inflated balloon surface. Typically, a micropipette can be used, as described above for the coating of the folded balloons. The same protocol can be followed, i.e. starting delivery of the solution from the mid of the balloon length and moving to an end of the balloon, then to the opposite end, while the balloon is rotated. It is important that substantially the whole balloon surface is wetted.

Preferably, the rotation of the balloon is not too fast. Typically, a rotational speed of the balloon during coating from about 5 rpm to about 30, preferably from about 10 rpm to about 20 rpm, is used, but different values may be set without departing from the scope of the invention. Preferably, the delivery time of the drug solution may range from about 10 seconds to about 500 seconds.

The rotation of the balloon may preferably be accomplished by means of a device as shown in FIG. 1 and as described below.

Step (d) or (j) of deflation of the coated balloon is accomplished by applying vacuum to the catheter balloon opening and/or by pressing the balloon from the exterior. Application of vacuum is preferred, in particular for long balloons.

Step (e) or (k) of folding and re-folding respectively is performed by means of conventional devices for folding balloons.

According to the processes mentioned above, folding (e) and re-folding (k) are performed when the balloon surface is still wet. This allows a better adherence of drug onto the balloon surface to be obtained.

Typically, the said folding (e) or re-folding (k) is performed within 20 minutes from the end of the coating step (c) or (i) respectively, preferably between 1 minute and 10 minutes, more preferably between 1 minute and 5 minutes.

If performed, step (f) or step (1) are accomplished by inserting over the folded or re-folded balloon a protective cover, typically a sleeve that envelops the balloon surface that has been coated with the drug. Such a sleeve is preferably made of a low friction material.

As a low friction material, polytetrafluoroethylene (PTFE) may conveniently be used. The use of a low friction material allows to minimize the removal of the drug adhered onto the balloon surface. The low friction material should have a friction coefficient below the friction coefficient of the material of which the balloon is made.

In general, independently from the method used, it is possible to repeat several times the balloon wetting step with the paclitaxel solution, as a function of the drug amount which is intended to be deposited.

As shown in FIG. 1, a suitable device for rotating a catheter balloon 2 is indicated with the numeral 1. The catheter balloon 2 comprises a catheter section 3 and a balloon section 4, that is shown in the inflated condition.

The device 1 comprises a basement 4, a first motor unit 5 and a second motor unit 6. Each motor unit 5, 6 comprises clamping means 8, 8' to clamp the two ends of the catheter balloon 2.

Preferably, the distal clamping means 8 acts upon the guide wire (not shown) on which the catheter balloon is loaded. Preferably, the proximal clamping means 8' acts upon the connector (luer) (not shown) the catheter balloon is provided with.

The motor units 5, 6 are preferably brushless motors. The motor units 5, 6 are synchronously operated. A command and control unit 7 provides for the synchronous operation of the two motor units 5, 6. This is important, in order to avoid torsion of the catheter balloon 2.

One or more supporting means 9, depending on the balloon length, are also provided in order to keep the catheter balloon 2 in an horizontal position.

According to another aspect, the invention relates to a catheter balloon completely or partially coated with paclitaxel in crystalline hydrated solvated form, having an immediate release and bioavailability of a therapeutically effective amount of paclitaxel at the site of intervention.

With "paclitaxel in crystalline hydrated solvated form" is meant paclitaxel with 2 to 3 molecules of water of crystallization and with 1 to 3 molecules of solvent.

It shall be noted that, both in the case of the hydrated crystalline form and the hydrated solvated crystalline form as defined before, paclitaxel tends to form dimers which take in water and/or the solvent into the crystalline structure. Therefore, it is possible that the number of molecules of water of crystallization or solvent into the solvate per molecule of paclitaxel is not defined by an integer, but by a decimal. For example, if a hydrated solvate is formed by crystallization from a solvent such as dioxane/water, a dimer can be obtained, which takes in 5 water molecules and 3 dioxane molecules: in this case, therefore, there will be 2.5 molecules of water of crystallization and 1.5 molecules dioxane per molecule of paclitaxel.

The crystalline hydrated solvated form of paclitaxel can be obtained from an aqueous solvent preferably selected from dioxane/water, DMF/water, DMSO/water, N-methylpyrrolidone/water, acetonitrile/water, N,N-dimethylacetamide/water, 1,3-dimethyl-3,4,5,6-tetrahydro-2-(1H)-pyrimidinone/water, 1,3-dimethyl-2-imidazolidinone/water mixtures, or mixtures thereof, by operating under suitable conditions, such as those described in the patent publication WO 03/0475078 in the name of Bristol-Myers Squibb Co., the content of which, relatively to such preparation methods, is incorporated herein by reference.

The preparation modes of the balloon completely or partially coated with paclitaxel in crystalline hydrated solvated form are completely similar to those described above for the hydrated crystalline form; therefore, they will not be further described.

According to a further aspect of the invention, a catheter balloon completely or partially coated with paclitaxel in crystalline hydrated or crystalline solvated hydrated form, having an immediate release and bioavailability of a therapeutically effective amount of paclitaxel at the site of intervention, can be obtained by dissolving paclitaxel in an aqueous solvent, as defined before, in the presence of urea, by completely or partially wetting the balloon surface with such solution, and by letting the solvent to evaporate to the formation of a crystalline layer having a white, homogeneous, or partially inhomogeneous appearance.

It has been noticed that the presence of urea in the coating layer of paclitaxel on the balloon surface promotes the release of the drug from such surface. Urea can be used in amounts ranging between 1 and 100 mg per mL solvent, preferably between 4 and 10 mg per mL solvent, more preferably about 7 mg per mL solvent.

It is a further object of the present invention a catheter balloon completely or partially coated with paclitaxel in crystalline hydrated or crystalline solvated hydrated form, having an immediate release and bioavailability of a therapeutically effective amount of paclitaxel at the site of intervention, in which said balloon is made of a polyether-polyamide block copolymer or "compound" thereof with a polyamide.

The polyether-polyamide block copolymer according to the invention is an elastomer comprising polyamide block-forming monomers, representing the hard portion of the material, modified with a group representing the soft portion.

This elastomer is obtained by polymerization of a polyamide block-forming compound selected from the group consisting of an aminocarboxylic acid according to the formula (1) and a lactam according to the formula (2):

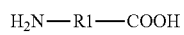   (1)

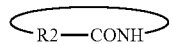   (2)

with a triblock polyetherdiamine compound of formula (3):

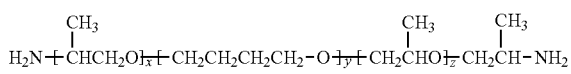   (3)

and with a dicarboxylic acid according to the formula (4):

$$HOOC—(R3)_m—COOH \quad (4)$$

In the above-mentioned formulae, each of the R1, R2, and R3 groups represents linking groups comprising a hydrocarbon chain therein, optionally interrupted by one or more amide groups.

Preferably, R1 and R2 independently comprise an alkylene group having 2 to 20 carbon atoms and amide bonds, and R3 comprises an alkylene group having 1 to 20 carbon atoms;

x can vary between 1 and 20, preferably between 1 and 18, more preferably between 1 and 16; y can vary between 4 and 50, preferably between 5 and 45, more preferably between 8 and 30, and z can vary between 1 and 20, preferably between 1 and 18, more preferably between 1 and 12;

m is 0 or 1.

Generally, the polymerization is carried out by using 15 to 70% by weight of the compound of formula (1) and/or (2), and a mixture of compounds of formulae (3) and (4) in an overall weight percentage between 30 and 85%. This polymerization is carried out in a reactor at a temperature ranging between 150 and 300° C., preferably between 160 and 280° C., more preferably between 180 and 250° C.

Compounds of such copolymers with polyamides can be obtained by mixing, according to known techniques, the copolymer in amounts from 10 to 90% by weight, preferably 75 to 25%, more preferably 60 to 40% by weight, with an amount of polyamide to completion of 100%.

Preferably, the polyamide is polyamide-12.

Such copolymers and the compounds thereof with polyamides are known, and have been described in detail in the patent publication WO 2007/132485 A1, the content of which, relatively to the structure of such materials, and obtaining thereof, is incorporated herein by reference.

It has been observed that the use of such material in the construction of the catheter balloon of the invention provides optimal characteristics of paclitaxel release, while balancing the necessary ability of retaining the drug during the processing and use steps far from the site of intervention with the easiness to release the paclitaxel layer to the vascular cell wall in the short contact time between this and the inflated balloon surface, at the site of intervention.

It is a further object of the present invention a catheter balloon completely or partially coated with paclitaxel in crystalline hydrated or crystalline solvated hydrated form, having an immediate release and bioavailability of a therapeutically effective amount of paclitaxel at the site of intervention, in which said balloon is made of polyamide-12.

It is a further object of the present invention a catheter balloon completely or partially coated with paclitaxel in crystalline hydrated or crystalline solvated hydrated form, having an immediate release and bioavailability of a therapeutically effective amount of paclitaxel at the site of intervention, in which said balloon is made of polyester amide.

The polyester amide used in the present invention can be described by the following general formula:

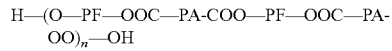

in which PA is a polyamide segment, PF is a diol segment comprising OH-terminating dimer diol segments, and n is a number ranging between 5 and 20.

The content of the diol component within the polyester-amide copolymer is 5-50% by weight. Preferably, the concentration of the diol component ranges between 10 to 30% by weight, still more preferably between 10 and 20% by weight of the total formulation.

These polymers are known, and have been described in detail in the patent publication WO 2005/037337 A1, the content of which, relatively to the chemical structure and the preparation methods of such materials, is incorporated herein by reference.

It is a further object of the present invention a catheter balloon completely or partially coated with paclitaxel in crystalline hydrated or crystalline solvated hydrated form, having an immediate release and bioavailability of a therapeutically effective amount of paclitaxel at the site of intervention, in which said balloon has a surface which is hydrophilic or hydrophilized by suitable hydrophilizing treatment.

For example, the catheter balloon surface according to the invention can be made hydrophilic by treatment with plasma-activated oxygen.

In all the above-described embodiments, paclitaxel is present in the catheter balloon coating layer in amounts ranging between 1 and 20 μg/mm², preferably between 2 and 7 μg/mm², more preferably between 3 and 5 μg/mm².

The invention will now be further described by means of the following examples, given by way of non-limiting example.

Example 1A—Coating of Catheter Balloons with Crystalline Hydrated or Crystalline Hydrated Solvated Paclitaxel Paclitaxel solutions have been prepared at a 50 mg/mL concentration in the following solvents:
(1) 9:1 THF/water
(2) 9:1 THF/water with addition of 15 mg/mL urea
(3) 6.5:3.5 THF/water
(4) Acetone/ethanol/water
(5) Acetic acid (comparative solution)
(6) Dichloromethane (comparative solution)

It shall be noted that paclitaxel in a crystalline hydrated or solvated hydrated form according to the invention is not obtained by crystallization from acetic acid. Instead, amorphous paclitaxel is obtained by precipitation from dichloromethane.

Some balloons—made of a polyamide-12+polyetherpolyamide block copolymer compound (70% UBESTA® XPA9063+30% UBESTA® 3030XA) and in a folded condition—have been coated with paclitaxel by wetting the surface thereof with equal volumes of the solutions (1)-(6) by means of a Hamilton syringe, according to the previously described modes. For each solution, several balloons have been used.

Then, the balloons have been dried under vacuum.

The appearance of the coating was white, not always homogeneous.

Example 1B—Coating of Catheter Balloons with Crystalline Hydrated or Crystalline Hydrated Solvated Paclitaxel (Coating in an Unfolded Condition)

The procedure of example 1A has been repeated using coating solution (2), by inflating first the folded balloons at 7 bar, then removing the pressurised air source and coating the inflated balloons by means of a Hamilton syringe. The coated balloons have then been re-folded after about 1 minute after the coating step, while the surface thereof was still wet.

The appearance of the coating was white, substantially homogeneous.

Example 2—Assessment of Paclitaxel Adhesion on the Surface of the Catheter Balloons The balloons prepared according to the example 1 have been subjected to some assessments, in order to determine the drug adhesion under the various conditions.

Test A

First, the dry adhesion has been assessed, which is useful to determine the paclitaxel loss which can occur in the production or handling steps of the balloon. Such determination has been carried out by dry expanding the balloon and shaking the inflated balloon within a tube.

The paclitaxel content in the tube was determined by HPLC/UV. The drug was taken up with ethanol, the tubes were closed and vigorously vortexed for at least 30 seconds, followed by a treatment in an ultrasound bath for 30 minutes. At least 70 μl of extract were injected into the HPLC, together with a paclitaxel standard solution (concentration of about 20 μg/mL). The results are reported in Table I.

Test B

Release of paclitaxel at the site of intervention has been assessed in experiments on castrated male pigs, approximately 3 months old, and weighing about 30 kg. The pigs were sedated by intramuscular injection of ketamine and xylazine. Anaesthesia was started by intravenous injection of propofol, followed by orotracheal intubation, and was maintained with 1-2 vol % isoflurane, vol % $N_2O_2$, and 30 vol % oxygen. All the animals received 5.000 IU heparin, 250 mg aspirine, and 200 mg nitroglicerine via the intracoronary route. The coronary arteries were monitored by means of a standard angiography technique through the left carotid artery.

The animals were treated with the paclitaxel-coated balloons (solutions (1)-(6)) mounted on catheter.

Some balloons, once the site of intervention has been reached, were kept floating in the blood flow for 1 minute without expanding them, then they were retracted, introduced into suitable tubes, inflated, and separated from the catheter. After that, they were extracted with ethanol as described in test A, and finally subjecting the tube to centrifugation for 10 minutes. The extracts were analyzed by HPLC/UV as previously described, so as to determine the paclitaxel amount which is dispersed in the blood flow. The results are reported in Table I.

Other balloons, on which stents had been mounted, have instead been introduced, inflated, and then deflated and retracted, then undergoing the same extraction treatment of those non-inflated. In this case, the residual paclitaxel amount left on the balloon after contacting the vessel wall was determined.

After a period of time ranging between 15 and 25 minutes, the animals were sacrificed by administration of 20% KCl under deep anaesthesia. Hearts were quickly removed, and the arterial segments on which the stent was arranged, plus a portion 5 mm down- and upstream the stent, were sectioned, placed in pre-weighted tubes to determine the weight thereof, and subjected to extraction with a predetermined amount of ethanol to achieve a >50% concentration. After 30 minutes of extraction at room temperature with ultrasounds and centrifugation for 10 minutes, the extracts were analyzed by HPLC/UV as described before, so as to determine the paclitaxel amount absorbed by the vascular tissue. The results are reported in Table I.

TABLE I

Results of drug adhesion, release, and uptake by the vascular tissue

| Deposition solution | % paclitaxel lost by dry expansion | % paclitaxel lost in blood flow (non-inflated balloon) | % paclitaxel not released to the site of intervention | % paclitaxel absorbed by the vascular tissue |
|---|---|---|---|---|
| (1) | 4 ± 3 | 22 ± 3 | 32 ± 9 | 13.3 ± 7.3 |
| (2)/EX. 1A | 24 ± 1 | 42 ± 3 | 13 ± 3 | 19.7 ± 11.3 |
| (2)/EX. 1B | 7 ± 4 | 27 ± 17 | 16 ± 8 | 17.7 ± 11.9 |
| (3) | 10 ± 5 | 26 ± 11 | 30 ± 6 | 17.4 ± 5.5 |
| (4) | 11 ± 11 | 33 ± 13 | 9 ± 4 | 23.4 ± 8.1 |
| (5) | 3 ± 2 | 5 ± 4 | 64 ± 5 | 5.2 ± 3.2 |
| (6) | 4 ± 3 | 41 ± 26 | 11 ± 7 | 17.4 ± 7.2 |

Data reported in Table I show that paclitaxel release is noticeably higher when the drug is present in crystalline hydrated or solvated hydrated form (lines (1) to (4)) compared to the non-hydrated form (line (5)). In fact, in the latter case, most paclitaxel (64%±5%) remains adhered to the balloon surface, and the drug amount absorbed by the vascular tissue is only 5.2%±3.2%.

As regards paclitaxel in the amorphous form (line (6)), although data show a high amount of drug released by the balloon and absorbed into the tissues, further experiments for the restenosis inhibition assessment demonstrated an inactivity of such form. In such further experiments, paclitaxel in crystalline hydrated or solvated hydrated form (lines (1)-(4)) exhibited, instead, a restenosis inhibition action in the animal.

Data also show that the presence of urea in the deposition solution (line (2)) produces a higher paclitaxel release and a higher amount of drug absorbed in the vascular tissue, compared to the same solution without the presence of urea (line (1)).

The coating in the inflated state, followed by re-folding while still wet, allows a better adherence of the drug onto the balloon surface.

Further investigations demonstrated that the material of which the balloon is made has also a considerable impact on the paclitaxel release properties, the polyether-polyamide block copolymer, or the compound thereof with polyamides giving the best results for drug elution.

Example 3—Determination of the Crystalline Form of Paclitaxel

Paclitaxel in crystalline hydrated form was identified by IR analysis under the conditions reported in the literature, thus obtaining a spectrum which was equivalent to what has been described in Jeong Hoon Lee et al., Bull. Korean Chem. Soc. 2001, vol. 22, No. 8, 925-928.

The invention claimed is:

1. A catheter balloon coated with paclitaxel in crystalline form, having an immediate release and bioavailability of a therapeutically effective amount of paclitaxel at a site of intervention, wherein:
the paclitaxel is present in a catheter balloon coating layer that does not comprise a polymer, and
the paclitaxel consists essentially of (i) paclitaxel in crystalline hydrated form, (ii) paclitaxel in crystalline hydrated solvated form, or (iii) paclitaxel in crystalline hydrated form and paclitaxel in crystalline hydrated solvated form,
wherein the coating layer comprises urea.

2. The catheter balloon of claim 1, wherein the coating layer consists essentially of (i) paclitaxel in crystalline hydrated form, (ii) paclitaxel in crystalline hydrated solvated form, or (iii) paclitaxel in crystalline hydrated form and paclitaxel in crystalline hydrated solvated form.

3. The catheter balloon of claim 1, wherein the paclitaxel comprises paclitaxel in crystalline hydrated form.

4. The catheter balloon of claim 3, wherein the crystalline hydrated form comprises water of crystallization in a molar ratio expressed by an integer or a decimal ranging between 2 and 4 per molecule of paclitaxel.

5. The catheter balloon of claim 1, wherein the paclitaxel comprises paclitaxel in crystalline hydrated solvated form.

6. The catheter balloon of claim 5, wherein the crystalline hydrated solvated form comprises water of crystallization in a molar ratio expressed by an integer or a decimal from 2 to 3, and solvating solvent in a molar ratio expressed by an integer or a decimal from 1 to 3 per molecule of paclitaxel.

7. The catheter balloon of claim 1, wherein the paclitaxel is present in a catheter balloon coating layer in amounts ranging between 1 and 5 µg/mm².

8. The catheter balloon of claim 1, wherein the release of a therapeutically effective amount of the paclitaxel occurs in a period of time ranging between 1 second and 1.5 minutes.

9. The catheter balloon of claim 1, wherein the bioavailability of the therapeutically effective amount of the paclitaxel occurs in periods of time ranging between 1 second and 25 minutes.

10. The catheter balloon of claim 1, wherein the coating layer is deposited on the balloon in a zigzag path.

11. The catheter balloon of claim 1, wherein the balloon comprises a polyether-polyamide block copolymer, or compound thereof with a polyamide.

12. The catheter balloon of claim 1, wherein the balloon is made of polyamide-12.

13. The catheter balloon of claim 1, wherein the balloon is made of polyester amide.

14. The catheter balloon according to claim 1, wherein the balloon has a surface which is hydrophilic or hydrophilized by suitable hydrophilizing treatment.

15. The catheter balloon of claim 1, wherein the paclitaxel is only present in the catheter balloon coating layer that does not comprise a polymer.

16. A method comprising:
dissolving paclitaxel in an aqueous solvent so as to form a paclitaxel solution, wherein the paclitaxel consists essentially of (i) paclitaxel in crystalline hydrated form, (ii) paclitaxel in crystalline hydrated solvated form, or (iii) paclitaxel in crystalline hydrated form and paclitaxel in crystalline hydrated solvated form, and wherein the paclitaxel solution does not comprise a polymer;
wetting a surface of a balloon catheter with the paclitaxel solution; and
allowing the solvent to evaporate to form a catheter balloon coated with paclitaxel in crystalline form, having an immediate release and bioavailability of a therapeutically effective amount of paclitaxel at a site of intervention,
wherein the paclitaxel solution further comprises urea.

17. The method of claim 16, wherein the aqueous solvent is selected from acetone/ethanol/water, tetrahydrofuran/water, methanol/water, acetone/water, ethanol/water, acetonitrile/water, DMF/water mixtures for crystalline hydrated paclitaxel, and from dioxane/water, DMF/water, DMSO/water, N-methylpyrrolidone/water, acetonitrile/water, N,N-dimethylacetamide/water, 1,3-dimethyl-3,4,5,6-tetrahydro-2-(1H)-pyrimidinone/water, 1,3-dimethyl-2-imidazolidinone/water mixtures, or mixtures thereof, for crystalline hydrated solvated paclitaxel.

18. The catheter balloon of claim 17, wherein the aqueous solvent for the formation of paclitaxel in crystalline hydrated form is selected from a 9:1 tetrahydrofuran/water mixture, or a tetrahydrofuran/water mixture with ratios ranging between 9.5:0.5 and 65:35, or an acetone/ethanol/water mixture, in which the organic solvent is present in an amount not less than 50% by volume relative to water.

19. The method of claim 16, wherein the paclitaxel solution comprises urea in an amount between 1 and 100 mg/mL.

20. The method of claim 16, wherein the paclitaxel solution comprises a concentration between 4 and 6 mg/ml of paclitaxel.

* * * * *